United States Patent [19]
Fogel

[11] Patent Number: 6,126,949
[45] Date of Patent: Oct. 3, 2000

[54] DI-BEHENYL FUMARATE AND ITS USE IN DERMATOLOGICAL PRODUCTS

[75] Inventor: Arnold W. Fogel, Upper Saddle River, N.J.

[73] Assignee: Bernel Chemical Company, Inc., Englewood, N.J.

[21] Appl. No.: 09/056,185

[22] Filed: Apr. 6, 1998

[51] Int. Cl.[7] .............................. A61K 7/00; A61K 7/021; A61K 7/06; A61K 7/50; A61K 7/48
[52] U.S. Cl. ........................ 424/401; 424/63; 424/70.1; 510/156; 510/159; 510/426
[58] Field of Search ................... 424/401, 70.1, 424/63; 510/156, 159, 426

[56] References Cited

U.S. PATENT DOCUMENTS

| | | | |
|---|---|---|---|
| 3,687,883 | 8/1972 | Korf | 260/29.6 |
| 4,074,978 | 2/1978 | Panzer | 44/62 |
| 4,184,978 | 1/1980 | France et al. | 252/309 |
| 4,228,151 | 10/1980 | Lang et al. | 424/59 |
| 4,534,963 | 8/1985 | Gordon | 424/69 |
| 5,025,004 | 6/1991 | Wu et al. | 514/165 |
| 5,221,286 | 6/1993 | Singleton | 8/406 |
| 5,436,006 | 7/1995 | Hirose et al. | 424/401 |
| 5,451,254 | 9/1995 | Andrean et al. | 106/503 |
| 5,476,648 | 12/1995 | Fogel | 424/59 |
| 5,525,588 | 6/1996 | Michetti | 512/4 |
| 5,658,575 | 8/1997 | Ribier et al. | 424/401 |
| 5,660,865 | 8/1997 | Pedersen et al. | 426/99 |
| 5,674,475 | 10/1997 | Dahms et al. | 424/59 |
| 5,690,918 | 11/1997 | Jacks et al. | 424/64 |
| 5,785,979 | 7/1998 | Wells | 424/401 |

*Primary Examiner*—John Kight
*Assistant Examiner*—D. Faulkner
*Attorney, Agent, or Firm*—Henry D. Coleman; R. Neil Sudol

[57] ABSTRACT

The present invention relates to novel anhydrous or water-in-oil synthetic ester compositions which are used in formulating dermatological products having uniform structure ranging in consistency from a soft gel to a hard stick. The compositions comprise a new component, dibehenyl fumaric acid ester, which has a melting point of approximately 72–74° C. The dibehenyl fumaric acid ester component has exceptional benefits when used in combination with any cosmetically acceptable oil in varying ratios, to produce homogeneous materials having a uniform structure. The di-behenyl fumaric acid ester according to the present invention may be used to harden or stiffen any cosmetically acceptable oil or water-in-oil emulsions and can be used to create compositions varying widely in viscosity and/or hardness from gels to solid systems such as sticks or to enhance the stability of water-in-oil emulsions. The compositions according to the present invention are particularly useful as additives in dermatological products, including cosmetic compositions and can accommodate components which vary widely in hydrophobicity or hydrophilicity.

21 Claims, No Drawings

DI-BEHENYL FUMARATE AND ITS USE IN DERMATOLOGICAL PRODUCTS

FIELD OF THE INVENTION

The present invention relates to novel anhydrous or water-in-oil synthetic ester compositions which are used in for mulating dermatological products having uniform structure ranging in consistency from a soft gel to a hard stick. The compositions comprise a new component, dibehenyl fumaric acid ester, which has a melting point of approximately 72–74° C. The dibehenyl fumaric acid ester component has exceptional benefits when used in combination with any cosmetically acceptable oil in varying ratios as set forth in greater detail herein, to produce unexpectely homogeneous materials having a uniform structure. The dibehenyl fumaric acid ester according to the present invention may be used to harden or stiffen any cosmetically acceptable oil or water-in-oil emulsions and can be used to create compositions varying widely in viscosity and/or hardness from gels to solid systems such as sticks. The compositions according to the present invention are particularly useful as additives in dermatological products, including cosmetic compositions. Quite unexpectedly, the compositions according to the present invention are characterized by uniform structure and homogeneity and for widely varying use as to produce gels or solid systems (sticks). The homogeneous, uniform structure compositions according to the present invention are used to produce superior properties in personal care products, e specially cosmetic products.

BACKGROUND OF THE INVENTION

The present invention emerged from ongoing research activity since 1957. In the late 1950's, the present inventor made oil-in-water emulsions using components such as cetyl palmitate, glycerol monostearate, soap, mineral oil, water dispersible gums and spermacetti (obtained from the sperm whale) as thickeners. The inventor also used thickeners such as paraffin, ozokerite, beeswax, cetyl alcohol, spermacetti and petrolatum in water-in-oil emulsions. In the 1960's, as a consequence of the natural product spermacetti no longer being available, certain of the above-described products could no longer be used, and substitutes had to be created. In 1985, the present inventor introduced stearyl stearate to harden an oil-in-water emulsion system and later commercialized the product under the name Hetester® 412. Much later, the present inventor worked with the composition behenyl behenate as a possible oil and/or water-in-oil emulsion hardener, but the compound was too waxy and hard and could be utilized effectively only in oil-in-water systems, not water-in-oil systems. The failure of behenyl behenate in water-in-oil emulsion systems started the present inventor on a search for an ester thickener to be used in lieu of paraffin and other natural-type waxes for thickening the oil phase of a water-in-oil emulsion.

Early on in the recent genesis of the instant invention, research centered on the introduction of a liquid emollient dicapryl maleate ("DCM"). With the success of DCM, the next derivative synthesized was a $C_{12}$–$C_{15}$ alkyl maleate, which also was a liquid, but had a 0° C. cloud point (the cloud point of DCM is −30° C.). During these research efforts, the present inventor learned that maleate esters will rearrange to fumarate esters, but fumarate esters will not rearrange to maleate esters. Consequently, the present inventor made the $C_{12}$–$C_{15}$ fumarate ester, instead of the $C_{12}$–$C_{15}$ maleate ester, which unexpectedly produced a solid material which melts at body temperature (about 37–39° C.). That discovery, which provides for a novel emollient composition having favorable melting characteristics at approximately body temperature, is the subject matter of a United States patent application. These products have be en marketed for several years.

In addition to the $C_{12}$–$C_{15}$ fumarate ester, $C_8$, $C_{16}$, $C_{18}$ and $C_{20}$ fumarates have been made with excellent safety, emolliency and other favorable characterisitics. These derivatives, other than the $C_8$ derivative, have not been marketed to date.

In conducting further research, the present inventor has discovered the highest melting point solid fumaric acid ester (di-behenyl fumarate) which is compatible with high molecular weight oils such as di-octyldodecyl ($C_{20}$) fumarate and di-decyltetradecyl ($C_{24}$) fumarate. Di-behenyl fumarate has a melting point of about 72–74° C. Utilizing a combination of the di-behenyl fumarate with any cosmetically acceptable emollient oil, the present inventor has d is covered compositions which may be prepared exhibiting a range of viscosity from soft gels to hard sticks, thus providing superior flexibility in formulation. Whether thickening oils only or thickening the oil phase of a water-in-oil emulsion, the resulting combination(s) is (are) uniform in structure, i.e., the di-behenyl fumarate is soluble in the oil phase in all proportions and hardens with equal distribution of the high melting point ester. The result is a uniform, homogeneous product of enhanced stability.

OBJECTS OF THE INVENTION

It is an object of the invention to provide formulations which may be utilized in dermatological compositions to provide stiffening or hardening to anhydrous emollient oils or water-in-oil emulsions.

It is an additional object of the invention to provide a composition which has sufficient flexibility to harden or stiffen anhydrous emollient oils or water-in-oil emulsions in order to produce compositions of varying viscosity including gels and sticks.

It is still another object of the invention to provide a method for stiffening or hardening an anhydrous emollient oil or water-in-oil emulsion to provide flexibility in the formulation of dermatological products, including cosmetics.

These and other objects of the present invention may be readily gleaned from the detailed description of the present invention which follows.

BRIEF DESCRIPTION OF THE INVENTION

The present invention relates to the use of the compound di-behenyl fumarate to harden or stiffen an anhydrous emollient oil or a water-in-oil emulsion. Di-behenyl fumarate is a compound of the structure:

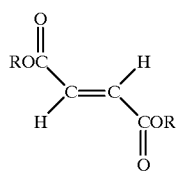

Where R is a $C_{22}H_{45}$ straight-chained alkyl group preferably derived from behenyl alcohol, $C_{22}H_{45}OH$.

In an anhydrous aspect of the present invention, the di-behenyl fumarate is formulated in combination with an emollient oil to produce a composition comprising about 10% to about 60% by weight of di-behenyl fumarate and about 40% to about 90% by weight of at least one emollient oil. The above-described compositions according to the present invention are useful alone or as a base formulation for dermatological formulations. Additional components which may be added to the di-behenyl fumarate/emollient oil composition to produce dermatological compositions according to the present invention include, for example, surfactants, skin and hair conditioning agents, coloring agents/pigments, fragrances, humectants, preservatives, anti-oxidants and oil soluble "actives" and medicaments, including vitamins, among numerous additional additives, including deodorant compounds, anti-perspirant compounds, including salts, among others.

In this aspect of the present invention, compositions according to the present invention will vary in the amount of di-behenyl fumarate included, as a function of the viscosity or stiffness/hardness desired in the formulation. Methods for stiffening or hardening emollient oils are clearly contemplated by the present invention. Compositions which contain di-behenyl fumarate in an amount ranging from about 10% to about 25% by weight of the formulation will tend to be in the form of a gel, whereas as the amount of di-behenyl fumarate increases within the two-component composition up to a level approaching approximately 40–60% by weight, the composition will stiffen into a semi-solid formulation which is advantageously utilized in stick formulations, such as lipsticks and deodorants. In compositions comprising di-behenyl fumarate within the range of about 25% to about 40%, the visocity tends to range from a viscous gel to a soft semi-solid.

In an aqueous aspect of the present invention, di-behenyl fumarate may be utilized as a stiffening/hardening agent in water-in-oil emulsions, such compositions comprising approximately 0.5% to about 40% by weight of di-behenyl fumarate and about 60% by weight to about 99.5% by weight of a water-in-oil emulsion, said water-in-oil emulsion comprising approximately 20–25% to about 55–60% by weight of water and about 40–45% to about 75–80% by weight of an emollient oil, said the water-in oil emulsion composition further including an amount of an emulsifying agent or emulsifier effective to form a water-in-oil emulsion from said water and said oil. Preferably, the amount of water included in this aspect of the present invention ranges from about 30% to about 50% by weight of the water-in-oil emulsion and the amount of oil included ranges from about 50% to about 70% by weight, with the emulsfier comprising the remaining amount of the water-in-oil emulsion composition effective to produce an emulsion, generally about 0.5% to about 15%, more preferably about 1% to about 10% by weight of the water-in-oil emulsion. In certain preferred aspects of the present invention, the ratio of the amount of water to oil in the water-in-oil emulsions is about 1:2. Compositions according to this aspect of the present invention range in viscosity from a flowing gel to a stick. Methods for stiffening/hardening water-in-oil emulsion compositions utilizing di-behenyl fumarate are also clearly contemplated by the present invention.

DETAILED DESCRIPTION OF THE PRESENT INVENTION

The following terms shall be used throughout the specification to describe the present invention.

The term "emollient oil" or "oil" is used throughout the specification to describe any of various lubricious, hydrophobic and combustible substances obtained from animal, vegetable and mineral matter. Emollient oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, the use of the terms "non-polar" and "polar" are relative within this very hydrophobic and lipophilic class, and all of the oils tend to be much more hydrophobic and lipophilic than the water phase which is used to produce the water-in-oil emulsion of the present invention. Preferred hydrophobic oils for use in the present invention include mineral oil and petrolatum. Preferred less hydrophobic (i.e., more polar) oils for use in the present invention include a number of maleates, neopentanoates, neopentanoyls, citrates and fumarates, and any other cosmetically acceptable ester emollient.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmacuetical products. Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

Preferred oils include petrolatum, mineral oil and certain "polar" oils such as synthetic emollient esters, among numerous others. The inclusion of petrolatum and/or mineral oil and/or the ratio of petrolatum to mineral oil in the present compositions will greatly influence the final viscosity of the water-in-oil compositions according to the present invention as will the amount or concentration of di-behenyl fumarate included within the water-in-oil compositions. It is a particularly unexpected aspect of the present invention that the inclusion of di-behenyl fumarate within the water-in-oil emulsion compositions according to the present invention would dramatically influence the viscosity of the emulsions. It is particularly surprising that di-behenyl fumarate could be included within water-in-oil emulsions and stiffen or harden these compositions in a manner which can produce compositions ranging in viscosity from a gel to a stick. "Stiffened" water-in-oil compositions according to the present invention provide unique characteristics in that the formulations will contain a water (hydrophilic) phase as well as an oil (hydrophobic phase), the result being that the stiffened water-in-oil emulsions according to the present invention will be useful in a variety of applications and may accommodate additives which greatly differ in hydrophilicity/ hydrophobicity. By thickening the outer phase of the water-in-oil emulsion with di-behenyl fumarate, the emulsion becomes substantially more stable, because the di-behenyl fumarate prevents the internal phase of water from separating from the oil phase, i.e., the di-behenyl fumarate keeps the water inside the oil phase by enhancing the ability of the water-in-oil emulsifier to operate in a more thickened phase. This enhanced stability is an unexpected characteristic of water-in-oil emulsion compositions of the present invention.

The term "water-in-oil emulsion" is used throughout the specification to describe certain compositions which consist essentially of water, an emollient oil and an emulsifying agent or emulsifier. The term water-in-oil emulsion is used as it is generally known in the art. A water-in-oil emulsion according to the present invention comprises approximately 20–25% to about 55–60% by weight of water and about 40–45% to about 75–80% by weight of an emollient oil, the water-in oil emulsion composition further including an amount of an emulsifying agent or emulsifier effective to form a water-in-oil emulsion from the water and the oil. Preferably, the amount of water included in this aspect of the present invention ranges from about 30% to about 50% by weight of the water-in-oil emulsion and the amount of oil included ranges from about 50% to about 70% by weight (most preferably, with the water and oil included at a weight ratio of about 1:2), with the emulsfier comprising the remaining amount of the water-in-oil emulsion composition, generally about 0.5% to about 15%, more preferably about 1% to about 10% by weight of the water-in-oil emulsion.

An "emulsion" for purposes of describing the present invention is a cream or lotion which is generally formed by the suspension of a very finely divided liquid, in this case water, in another liquid, in this case, an oil. In the present invention, an emulsion is formed when the water phase is compatibilized in the oil phase using an emulsifier or emulsifying system, such that the water phase becomes "hidden" within the oil phase.

The term "emulsifying agent" or "emulsifier" is used throughout the specification to describe compounds which are added to the water and oil to produce water-in-oil emulsions according to the present invention. Emulsifiers as used generally are considered surfactants which exhibit good surface activity and produce a low interfacial tension in the system in which it is used. Emulsifiers preferably used in the present invention exhibit a tendency to migrate to the interface, rather than remain dissolved in either one of the water or emollient oil phase. Emulsifiers for use in the present invention have a balance of lipophilic and hydrophilic groups such that the emulsifier will distort the structure of both the oil and water phases to some extent, although not necessarily equally. Too great a solubility in either phase will result in poor or even no emulsion being formed. In addition, emulsifiers for use in the present invention preferentially are oil-soluble. Mixtures of emulsifiers may be preferred, especially where at least one of the emulsifiers is preferentially oil-soluble and at least one of the emulsifiers is preferentially water-soluble (or dispersible). In addition, the more polar the oil phase, for example, where the emollient oil is a synthetic ester, the more polar and hydrophilic the emulsifier should be. The more non-polar or lipophilic the emollient oil, the more lipophilic the emulsifier should be. This generalization is the basis for a number of methods for minimizing the work of selecting the most suitable emulsifier or combination of emulsifiers for a particular system. Among the methods for determining the suitability of an emulsifier or combination of emulsifier to be used in water-in-oil emulsions according to the present invention are the HLB method, the Pit method and the Maximum Solubilization Method. (See, for example, Chapter 8, "Emulsfication by Surfactants", in *Surfactants and Interfacial Phenomena*, Second Edition, by Milton J. Rosen, John Wiley & Sons). One of ordinary skill in the art may readily determine the type of emulsifier or emulsifying system (group of emulsifiers) which may be used in the water-in-oil emulsions according to the present invention.

Exemplary emulsifiers for use in the present invention may be non-ionic, anionic, cationic or amphoteric and include, but are not limited to, for example linear or branched chain alcoholic ethoxylates and ethoxysulfates, alcohol ethoxylates, polysorbate esters, ethoxylated alkylphenols, for example, polyethoxynonylphenols, phenoxypolyalkoxyalcohols, for example, nonylphenoxypoly(ethyleneoxy)ethanol and nonylphenoxypolyethoxyethanol, hydrophobic compounds such as ethylene oxide condensation products with higher fatty acids, higher fatty alcohols, or alkylated aromatic hydrocarbons, higher molecular weight poly propylene glycols, amide and amine condensation products of which N-bis(2-hydroxyethyl)-lauramide is exemplary. In particular, preferred emulsifiers include the nonylphenolethoxylate surfactants, which are obtained from the reaction product of ethylene oxide and nonylphenol. The number of moles of ethylene oxide reacted with nonylphenol determine the length of the polyethyleneoxide side chain, the hydrophilicity of the polyethyleneoxide side chain (the longer the chain, the more hydrophilic) and the overall hydrophilicity or hydrophobicity of the final surfactant compound used. Other preferred nonionic emulsifiers include polyoxyethylene ethers including polyoxyethylene isohexadecyl ether, such as Arlasolve™ 200 (available from ICI Americas), polyoxyethylene lauryl ether such as Brij 35™, polyoxyethylene stearyl ether, for example Brij 72™ and Brij 78™ and polyoxypropylenestearyl ether, for example, PPG-15 stearyl ether (Arlamol E, from ICI Americas). Other exemplary emulsifiers include ethoxylated lanolin, for example, Lanogel 41 (Amerchol, Inc. Edison, N.J.), alkyl and dialkyl succinate compounds, including combinations of these emulsifiers.

Exemplary anionic emulsifiers for use in the present invention include, for example, surfuric acid esters of polyhydric alochols, e.g. lauryl sulfate, cetyl sulfate, etc., higher fatty alcohol sulfates, such as those derived from cocoanut oil, hydroxyl sulfonated higher fatty acid esters such as fatty acid esters of 2,3-dihydropropane sulfonic acid, high fatty acid esters of low molecular weight alkylol sulfonic acids, e.g., oleic acid ester of isethionic acid, sulfated higher fatty acid alkylolamides such as ethanol amide sulfates, higher fatty acid amides of amine alkyl sulfonic acids, such as lauric amide of taurine, among others and armomatic containing anionic anionic synthetic emulsifiers. Exemplary amphoteric emulsifiers include, for example, salts of N-alkyl compounds of betaamino propionic acid wherein the alkyl group is derived from a fatty acid such as a mixture of cocoanut oil fatty acids, among others. Exemplary cationic surfactants include ammonium and quaternary salts of fatty amines and substituted fatty amines, among others. All of the above emulsifiers, among numerous others, may be used alone or in combination with other emulsifiers to make water-in-oil emulsions according to the present invention.

The term "uniform structure" is used throughout the present specification to describe compositions of the present invention. Compositions which have uniform structure are considered smooth and homogeneous. Compositions according to the present invention are non-crystalline, are not cheesy, and have a substantial absence of (preferably, are completely devoid of) air pockets. Compositions according to the present invention make smooth films. Compositions according to the present invention provide a uniform structure in a synthetic composition and quite unexpectedly can be used as a thickening or hardening agent. The dibehenyl fumarate compound of the present invention is soluble in all proportions in an emollient oil and consequently, as the oil and dibehenyl fumarate cool after a mixing step conducted at elevated temperature, the compounds harden together and produce a composition of uniform structure.

The term "stabilizing" or "stable" is used to describe the ability of the di-behenyl fumarate to reduce the tendency of the water-in-oil emulsions to separate out into distinct layers or phases after a period of time. Thus, in the present invention, a further aspect relates to the ability of the di-behenyl fumarate, in effective amounts, to stabilize the water-in-oil emulsions and reduce and/or prevent the water-in-oil emulsions from separating into a water phase and an oil phase. In preferred aspects of this aspect of the present invention, the amount of di-behenyl fumarate added to the water-in-oil emulsion will range from about 0.5% to about 15% by weight of the composition comprising a water-in-oil emulsion and di-behenyl fumarate.

The term "effective amount" is used throughout the specification, including the claims, to describe amounts or concentrations of individual components used in compositions according to the present invention for the purpose for which they are included in the present compositions. Thus, where an emulsifier is used, an "effective amount" of an emulsifier is that amount which is effective for emulsifying the composition described. Where an effective amount of dibehenyl fumarate is used in compositions according to the present invention, it is used in amounts effective to provide the characteristics sought by adding the component, i.e, some measure of viscosity increase without disadvantageously impacting other characteristics of the desired product. The term "stabilizing effective amount" is used to describe that amount of di-behenyl fumarate added to water-in-oil emulsion compositions according to the present invention which stabilize the emulsion, i.e. reduce or prevent the separation of the emulsion into distinct or separate water and oil phases.

There are two general aspects of the present invention, an anhydrous aspect and an aqueous aspect. In an anhydrous aspect of the present invention, the di-behenyl fumarate is formulated in combination with an emollient oil to produce a composition comprising about 10% to about 60% by weight of di-behenyl fumarate and about 40% to about 90% by weight of emollient oil, depending upon the relative viscosity of the formulations desired (gel, paste or stick). The above-described compositions according to the present invention are useful alone or as a base formulation for dermatological formulations. Additional components which may be added to the di-behenyl fumarate/emollient oil composition to produce dermatological compositions according to the present invention include, for example, surfactants, conditioning agents, coloring agents/pigments, fragrances, humectants, anti-perspirant salts, deodorant compounds, preservatives, anti-oxidants and actives and medicaments, including vitamins, among numerous additional additives.

In this aspect of the present invention, compositions which contain di-behenyl fumarate in an amount ranging from about 10% to about 25% by weight of the formulation will tend to be in the form of a gel, whereas as the amount of di-behenyl fumarate increases within the two-component composition up to a level approaching approximately 40–60% by weight, the composition will stiffen into a semi-solid formulation which is advantageously utilized in stick formulations, such as lipsticks and deodorants/antiperspirants. Compositions containing about 25% to about 40% by weight di-behenyl fumarate will have viscosities ranging from a viscous gel to a soft semi-solid.

In an aqueous aspect of the present invention, di-behenyl fumarate may be utilized as a stiffening/hardening and stabilizing agent in water-in-oil emulsions, such compositions comprising approximately 0.5% to about 40% by weight of di-behenyl fumarate and about 60% by weight to about 99.5% by weight of a water-in-oil emulsion, the water-in-oil emulsion comprising approximately 20–25% to about 55–60% by weight of water and about 45–50% to about 75–80% by weight of an emollient oil, the water-in oil emulsion composition further including an amount of an emulsifying agent or emulsifier effective to form a water-in-oil emulsion from said water and said oil, preferably within the range of about 0.5% and about 15% by weight of the combination of water, oil and emulsifier. Preferably, the amount of water included in this aspect of the present invention ranges from about 30% to about 50% by weight of the water-in-oil emulsion and the amount of oil included ranges from about 50% to about 70% by weight, with the emulsfier comprising the remaining amount of the water-in-oil emulsion composition, preferably in an amount ranging from about 1% to about 10% by weight of the water-in-oil emulsion.

Compositions according to the present invention may be made simply and with relative ease. In the case of anhydrous compositions, the solid dibehenyl fumarate may be added to the oil, preferably at elevated temperature (i.e., above about 75° C.) to the desired concentration. Upon vigorous mixing, the composition will be completely mixed and attain a consistency and homogeneity which will produce a formulation varying from a gel to a solid (stick) upon cooling to room temperature.

Having generally described the invention, reference is now made to the following examples which are intended to illustrate preferred embodiments and comparisons. The included examples are not to be construed as limiting the scope of this invention as is more broadly set forth above and in the appended claims.

EXAMPLES

Example 1

Synthesis of Dibehenyl Fumarate 2 moles of behenyl alcohol is reacted with 1 mole fumaric acid using standard ester manufacturing procedures (heated at 160–180° C. with 0.1% by weight of the reactants of a catalyst such as tin oxalate or dibutyl tin oxide) in inert solvent in standard manufacturing equipment until the production of water from the esterification is complete and an appropriate SAP value and acid value are reached. The compound is isolated by distilling off excess solvent, if present, extracting out the dibehenyl fumarate, or precipitating di-behenyl fumarate out of water, followed by recrystalliziation of the crude product/precipitate to provide di-behenyl fumarate which is used in the following examples.

Example 2

Anhydrous Cream Cleanser

| Compound | Percent By Weight |
|---|---|
| Dibehenyl fumarate | 25.0 |
| Marrix ® 220L (Bernel Chemical Englewood N.J.) (Di-octyldodecyl fumarate) | 65.0 |
| Marrix ® SF (Bernel Chemical Englewood N.J.) ($C_{12}$–$C_{15}$ alkyl fumarate) | 10.0 |

Procedure: heat and mix at 85° C. until clear.

Comments:

1. This gel is for cleansing, or alternatively, for facial coloring.
2. This base makes an excellent hair pomade or rouge.
3. If a washable base is desired, 20% of propylene glycol isoceteth 3-acetate (Hetester PHA) may be used and the liquid fumarate Matrix® 220 L may be lowered by 20%.

Example 3

Lipstick Base Formulation

| Compound | Parts By Weight |
|---|---|
| Dibehenyl fumarate | 50.0 |
| Marrix ® 220L (Di-octyldodecyl fumarate) | 50.0 |
| $TiO_2$ (40% in castor oil) | 9.0 |
| Yellow #5 (25% in castor oil) | 8.0 |
| Red #6 (25% in castor oil) | |
| Red #7 (25% in castor oil) | 3.0 |
| Blue #1 (25% in castor oil) | 1.0 |
| | 127.0 Parts Total |

Procedure: heat to 90° C. and mix well. Mold at 75° C.

Comments:

1. Compound of the present invention is an excellent thickener for creams and lotions to produce compositions varying in viscosity from gels to sticks.

Example 4

Water-in-Oil Cream Based upon Polar and Non-Polar Oils

The following components were combined in two separate phases, phase A, the oil phase and phase B, the water phase. After complete mixing of phases A and B, phase C was added at elevated temperature and mixed with the other components to produce a flowing lotion.

| | | Weight % |
|---|---|---|
| Phase A: (heat to 85° C. and mix) | "BSA" (1) | 2.30 |
| | DiBehenyl Fumarate | 8.00 |
| | White Petrolatum | 10.00 |
| | Mineral Oil (Kaydol) | 33.45 |
| | Di-2-Ethyl Hexyl Fumarate (2) | 10.00 |
| | DEA Cetyl Phosphate (amphisol) (3) | 0.50 |
| | Propyl Paraben | 0.10 |
| Phase B: (heat to 85° C.) | Water, deionized | 33.30 |
| | Borax | 1.10 |
| Phase C: (add to emulsion at 75–80° C.) | Fumed $SiO_2$ (cabosil) | 1.25 |
| | | 100.0% total |

(1) 12-Behenyl hydroxystearic acid (BSA)-prepared by reacting 1 mole of Behenic acid, 1 mole of 12-hydroxy stearic acid and 0.1% by weight dibutyl tin oxide (based upon the total weight of the reactants). These individual components were charged to a glass vessel equipped with proper mixer and a water trap to collect water. The components were mixed and heated at 200° C. until the desired saponification value, hydroxyl value and acid value are achieved. "Typical" Assay for BSA (not a specification)

sap value=161.5 acid value=104.5 hydroxyl value=7.5 color (melted)=gardner 2+ melting point=68° C.

(2) commercial as Bernel Ester 284 (Bernel Chemical Co. Englewood, N.J.)

(3) Amphisol available from Hoffmann-LaRoche, Nutley, N.J.

Procedure:

Add B to A at 85° C. Mix without aeration. Cool and add C at 75–80° C.; continue to mix until homogeneous and cool to approximately 55° C. Package at 55° C.

Note: the "BSA" 1 is the primary emulsifier, however, this emulsion uses 2 auxilliary emulsifiers with "BSA". They are amphisol and cabosil. The di-behenyl fumarate is functions to thicken or harden this composition.

Example 5

Synthetic Water-in-Oil Cream Based upon Polar Oils

The same procedure which was followed for Example 4 was essentially also followed here, with minor variation.

| | | Weight % |
|---|---|---|
| phase A: (mix at 85–90° C.) | "BSA" | 2.30 |
| | DiBehenyl Fumarate | 8.00 |
| | Di-$C_{12-15}$ Alkyl Fumarate (2) | 10.00 |
| | Di-decyltetradecyl ($C_{24}$) Fumarate (1) (Octyl Dodecyl NeoPentanoate) | 28.45 |
| | ELEFAC I-205 | 15.00 |
| | DEA Cetyl Phosphate (Amphisol) (3) | 0.50 |
| | Propyl Paraben | 0.10 |

-continued

| | | Weight % |
|---|---|---|
| phase B: (mix at 85–90° C.) | Water, deionized | 33.30 |
| | Borax N.F. | 1.10 |
| phase C: | Fumed SiO$_2$ (cabosil) | 1.25 |
| | | 100.0% total |

(1) obtained pursuant to preparation of BSA (example 3) or example 1 (di-behenyl fumarate) utilizing analogous conditions and reagents;
(2) commercial as Marrix ® SF (Bemel Chemical Co., Englewood, New Jersey);
(3) Hoffmann-LaRoche Procedure:
Add B to A at 85° C. and mix without aeration. Continue mixing while slowly adding C. Mix and cool to 50° C. Package.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. An anhydrous composition for use as a cream, stick or cosmetic base consisting essentially of about 10% to about 60% by weight of di-behenyl fumarate in combination with an emollient oil in an amount ranging from about 40% to about 90% by weight.

2. The composition according to claim 1 further including an effective amount of at least one additive selected from the group consisting of surfactants, skin and hair conditioning agents, coloring agents/pigments, fragrances, humectants, preservatives, anti-oxidants, medicaments including vitamins, anti-perspirant salts, deodorant compounds and mixtures, thereof.

3. The composition according to claim 1 wherein said emollient oil is selected from the group consisting of mineral oil, petroleum jelly and synthetic emollient esters.

4. The composition according to claim 3 wherein said synthetic emollient esters are maleate and fumarate esters other than di-behenyl fumarate.

5. The composition according to claim 4 wherein said fumarate ester is di-octyldodecyl (C$_{20}$) fumarate.

6. The composition according to claim 4 wherein said fumarate ester is di-C$_{12-15}$ alkyl fumarate.

7. The composition according to claim 1 wherein said additive is selected from the group consisting of hair conditioners, anti-perspirant salts, deodorant compounds and mixtures, thereof.

8. A composition for use as or in formulating a dermatological product comprising a water-in-oil emulsion in combination with di-behenyl fumarate, said di-behenyl fumarate consisting essentially of about 0.5% to about 40% by weight of said composition and said water-in-oil emulsion comprising about 60% by weight to about 99.5% by weight of said composition, said water-in-oil emulsion comprising about 20% to about 60% by weight water and about 40% to about 80% by weight of an emollient oil, said water-in-oil emulsion further including an amount of an emulsifier effective to form a water-in-oil emulsion from said water and said oil.

9. The composition according to claim 8 wherein said water-in-oil emulsion comprises about 30% to about 50% by weight water and about 50% to about 70% by weight emollient oil.

10. The composition according to claim 9 wherein said emulsifier is included in said water-in-oil emulsion in an amount ranging from about 1.0% to about 10% by weight.

11. The composition according to claim 9 wherein said water-in-oil emulsion comprises about water and oil in a weight ratio of about 1:2, said emulsion further comprising an effective amount of an emulsifier.

12. The composition according to claim 8 further including an effective amount of at least one additive selected from the group consisting of hair and skin conditioning agents, coloring agents/pigments, fragrances, humectants, preservatives, anti-oxidants, medicaments, including vitamins, anti-perspirant compounds, deodorant compounds and mixtures, thereof.

13. The composition according to claim 8 wherein said emollient oil is selected from the group consisting of mineral oil, petroleum jelly and synthetic emollient esters.

14. The composition according to claim 9 wherein said synthetic emollient esters are maleate and fumarate esters other than di-behenyl fumarate.

15. The composition according to claim 14 wherein said fumarate ester is di-octyldodecyl (C$_{20}$) fumarate.

16. The composition according to claim 14 wherein said fumarate ester is di-C$_{12-15}$ alkyl fumarate.

17. The composition according to claim 12 wherein said additive is selected from the group consisting of hair conditioning agents, medicaments, anti-perspirant compounds deodorant compounds and mixtures, thereof.

18. The composition according to claim 9 further including an effective amount of at least one additive selected from the group consisting of conditioning agents, coloring agents/pigments, fragrances, humectants, preservatives, anti-oxidants, medicaments, anti-perspirant compounds, deodorant compounds and mixtures, thereof.

19. A method of stabilizing a water-in-oil emulsion comprising including in said water-in-oil emulsion an amount of di-behenyl fumarate effective to stabilize said emulsion, said emulsion consisting essentially of about 20% to about 60% by weight water and about 40% to about 80% by weight of an emollient oil, said water-in-oil emulsion further including an amount of an emulsifier effective to form a water-in-oil emulsion from said water and said oil.

20. The method according to claim 19 wherein said water-in-oil emulsion comprises about 30% to about 50% by weight water and about 50% to about 70% by weight of an oil, said emulsifier comprising about 1% to about 10% by weight of said emulsion.

21. The method according to claim 19 wherein said di-behenyl fumarate is included in an amount ranging from about 0.5% to about 15% by weight of said composition which includes di-behenyl fumarate in said water-in-oil emulsion.

* * * * *